US006673770B1

(12) United States Patent
Wauben et al.

(10) Patent No.: US 6,673,770 B1
(45) Date of Patent: Jan. 6, 2004

(54) PEPTIDES FOR THE TREATMENT, PROPHYLAXIS, DIAGNOSIS AND MONITORING OF AUTOIMMUNE DISEASES

(75) Inventors: Marca Henriëtte Michaela Wauben, Almere (NL); Willem Van Eden, Bilthoven (NL)

(73) Assignee: Upither B.V., CL Utrecht (NL)

( * ) Notice: Subject to any disclaimer, the term of this patent is extended or adjusted under 35 U.S.C. 154(b) by 0 days.

(21) Appl. No.: 09/647,372

(22) PCT Filed: Mar. 30, 1999

(86) PCT No.: PCT/NL99/00189

§ 371 (c)(1), (2), (4) Date: Oct. 26, 2000

(87) PCT Pub. No.: WO99/50282

PCT Pub. Date: Oct. 7, 1999

(30) Foreign Application Priority Data

Mar. 30, 1998 (EP) ........................................ 98200993

(51) Int. Cl.$^7$ ........................ A61K 38/17; A61K 38/39; C07K 14/78; C07K 14/705; G01N 33/68

(52) U.S. Cl. .......................... 514/13; 435/7.24; 514/14; 514/15; 514/21; 530/326; 530/327; 530/328

(58) Field of Search ....................... 424/9.1, 9.2, 94.67; 435/7.24; 514/2, 8, 12, 13, 14, 15, 21; 530/326, 327, 328, 350

(56) References Cited

U.S. PATENT DOCUMENTS

| | | | | |
|---|---|---|---|---|
| 4,716,038 A | * 12/1987 | Stanford et al. | ......... | 424/195.1 |
| 4,772,557 A | * 9/1988 | Eisen et al. | ................. | 435/320 |
| 5,260,059 A | * 11/1993 | Acott et al. | .............. | 424/94.67 |
| 5,354,691 A | * 10/1994 | Van Eden et al. | .......... | 436/506 |
| 5,605,690 A | * 2/1997 | Jacobs et al. | ............ | 424/134.1 |

FOREIGN PATENT DOCUMENTS

| | | |
|---|---|---|
| EP | 322990 | * 7/1989 |
| EP | 685557 | * 12/1995 |
| WO | 97/11966 | * 4/1997 |
| WO | 98/32427 | * 7/1998 |

OTHER PUBLICATIONS

Goodacre et al. Human cartilage aggrecan CS1 region . . . Immunology. 1993, vol. 78, pp. 586–591.*

Phelps et al. Direct Identification of Naturally Processed Autoantigen . . . The Journal Of Biological Chemistry. Aug. 2, 1996, vol. 271, No. 31, pp. 18549–18553.*

Schuenke et al. Binding Specificity of a Class II–Restricted Hepatitis . . . Human Immunology. 1998, vol. 59, pp. 783–793.*

Phelps et al. Presentation of the Goodpasture Autoantigen . . . The Journal Of Biological Chemistry. May 8, 1998, vol. 273, No. 19, pp. 11440–11447.*

Anderton et al. Differential Mycobacterial 65–kDa Heat Shock Protein . . . Journal of Immunology. 194, vol. 152, pp. 3656–3664.*

Joosten et al. Direct binding of autoimmune disease . . . International Immunology. 1994, vol. 6, No. 5, pp. 751–759.*

* cited by examiner

*Primary Examiner*—Jeffrey E. Russel
(74) *Attorney, Agent, or Firm*—Sughrue Mion, PLLC

(57) ABSTRACT

The invention provides a peptide suitable for the prophylaxis, treatment, diagnosis or monitoring of arthritis. The peptide contains a contiguous sequence element of 9 amino acid residues (nonapeptide), having the amino acid sequence: X1-X2-X3-X4-X5-X6-X7-X8-X9. In the sequence, X2, X6 and X7 are any amino acid; X1 is any amino acid except K, H, R, E, D; X3 is S or T; X4 is one of F, L, I, V, A, G, C, P; X5 is one of A, G, C, P, S, N, T, V; X8 is one of V, L, I, M; and X9 is E or D. The peptide is also a part of a mammalian cartilage, joint or arthritis-related protein such as collagen or a cartilage protein, and is between 9–20 amino acids in length. Furthermore, the peptide is recognised by freshly isolated T cells from rats in which Adjuvant Arthritis is induced and/or is recognised in vitro by T cell clone A2*b*.

14 Claims, 1 Drawing Sheet

SEQUENCE LISTING

```
<160> NUMBER OF SEQ ID NOS: 81

<210> SEQ ID NO 1
<211> LENGTH: 5
<212> TYPE: PRT
<213> ORGANISM: Artificial Sequence
<220> FEATURE:
<223> OTHER INFORMATION: consensus sequence from DRB1

<400> SEQUENCE: 1

Gln Lys Arg Ala Ala
1               5


<210> SEQ ID NO 2
<211> LENGTH: 5
<212> TYPE: PRT
<213> ORGANISM: Artificial Sequence
<220> FEATURE:
<223> OTHER INFORMATION: consensus sequence from DRB1
```

-continued

```
<400> SEQUENCE: 2

Gln Arg Arg Ala Ala
1               5


<210> SEQ ID NO 3
<211> LENGTH: 9
<212> TYPE: PRT
<213> ORGANISM: Mycobacterium tuberculosis

<400> SEQUENCE: 3

Thr Phe Gly Leu Gln Leu Glu Leu Thr
1               5


<210> SEQ ID NO 4
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 4

Ala Phe Gly Leu Gln Leu Glu Leu Thr
1               5


<210> SEQ ID NO 5
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 5

Thr Ala Gly Leu Gln Leu Glu Leu Thr
1               5


<210> SEQ ID NO 6
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 6

Thr Phe Ala Leu Gln Leu Glu Leu Thr
1               5


<210> SEQ ID NO 7
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 7

Thr Phe Gly Ala Gln Leu Glu Leu Thr
1               5


<210> SEQ ID NO 8
<211> LENGTH: 9
<212> TYPE: PRT
<213> ORGANISM: Artificial sequence
<220> FEATURE:
```

-continued

```
<223> OTHER INFORMATION: Mycobacterial hsp65 180-188 alanine
      substitution analogue

<400> SEQUENCE: 8

Thr Phe Gly Leu Ala Leu Glu Leu Thr
1               5


<210> SEQ ID NO 9
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 9

Thr Phe Gly Leu Gln Ala Glu Leu Thr
1               5


<210> SEQ ID NO 10
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 10

Thr Phe Gly Leu Gln Leu Ala Leu Thr
1               5


<210> SEQ ID NO 11
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 11

Thr Phe Gly Leu Gln Leu Glu Ala Thr
1               5


<210> SEQ ID NO 12
<211> LENGTH: 9
<212> TYPE: PRT
<213> ORGANISM: Artificial sequence
<220> FEATURE:
<223> OTHER INFORMATION: Mycobacterial hsp65 180-188 alanine
      substitution analogue

<400> SEQUENCE: 12

Thr Phe Gly Leu Gln Leu Glu Leu Ala
1               5


<210> SEQ ID NO 13
<211> LENGTH: 9
<212> TYPE: PRT
<213> ORGANISM: Homo sapiens

<400> SEQUENCE: 13

Leu Lys Ser Leu Ser Gln Gln Ile Glu
1               5


<210> SEQ ID NO 14
<211> LENGTH: 9
<212> TYPE: PRT
```

-continued

<213> ORGANISM: Homo sapiens

<400> SEQUENCE: 14

Leu Lys Ser Leu Asn Asn Gln Ile Glu
1               5

<210> SEQ ID NO 15
<211> LENGTH: 9
<212> TYPE: PRT
<213> ORGANISM: Rattus sp.

<400> SEQUENCE: 15

Leu Lys Ser Val Asn Gly Gln Ile Glu
1               5

<210> SEQ ID NO 16
<211> LENGTH: 9
<212> TYPE: PRT
<213> ORGANISM: Homo sapiens

<400> SEQUENCE: 16

Ile Phe Ser Leu Thr Pro Val Leu Asp
1               5

<210> SEQ ID NO 17
<211> LENGTH: 9
<212> TYPE: PRT
<213> ORGANISM: Homo sapiens

<400> SEQUENCE: 17

Gln Ala Ser Gly Ser Ala Ile Ile Asp
1               5

<210> SEQ ID NO 18
<211> LENGTH: 9
<212> TYPE: PRT
<213> ORGANISM: Mus musculus

<400> SEQUENCE: 18

Gln Ala Ser Gly Ser Ala Ile Met Glu
1               5

<210> SEQ ID NO 19
<211> LENGTH: 9
<212> TYPE: PRT
<213> ORGANISM: Homo sapiens

<400> SEQUENCE: 19

Leu Lys Ser Leu Ser Ser Gln Ile Glu
1               5

<210> SEQ ID NO 20
<211> LENGTH: 9
<212> TYPE: PRT
<213> ORGANISM: Rattus sp.

<400> SEQUENCE: 20

Val Gly Ser Ala Ser Gly Ala Leu Asp
1               5

<210> SEQ ID NO 21
<211> LENGTH: 9
<212> TYPE: PRT
<213> ORGANISM: Rattus sp.

-continued

<400> SEQUENCE: 21

Leu Pro Ser Gly Gly Glu Ser Leu Glu
1 5

<210> SEQ ID NO 22
<211> LENGTH: 9
<212> TYPE: PRT
<213> ORGANISM: Rattus sp.

<400> SEQUENCE: 22

Leu Pro Ser Gly Gly Asp Asp Leu Glu
1 5

<210> SEQ ID NO 23
<211> LENGTH: 9
<212> TYPE: PRT
<213> ORGANISM: Homo sapiens

<400> SEQUENCE: 23

Leu Arg Ser Pro Val Ile Ser Ile Asp
1 5

<210> SEQ ID NO 24
<211> LENGTH: 9
<212> TYPE: PRT
<213> ORGANISM: Mus musculus

<400> SEQUENCE: 24

Leu Arg Ser Pro Val Ile Ser Ile Glu
1 5

<210> SEQ ID NO 25
<211> LENGTH: 9
<212> TYPE: PRT
<213> ORGANISM: Homo sapiens

<400> SEQUENCE: 25

Gln Asp Thr Val Ser Leu Thr Val Asp
1 5

<210> SEQ ID NO 26
<211> LENGTH: 9
<212> TYPE: PRT
<213> ORGANISM: Rattus sp.

<400> SEQUENCE: 26

Val Ser Ser Phe Ser Leu Asn Val Glu
1 5

<210> SEQ ID NO 27
<211> LENGTH: 9
<212> TYPE: PRT
<213> ORGANISM: Homo sapiens

<400> SEQUENCE: 27

Ala Gly Thr Leu Ser Pro His Val Glu
1 5

<210> SEQ ID NO 28
<211> LENGTH: 9
<212> TYPE: PRT
<213> ORGANISM: Homo sapiens

<400> SEQUENCE: 28

-continued

Ser Ala Ser Ala Thr Tyr Gly Val Glu
1 5

<210> SEQ ID NO 29
<211> LENGTH: 9
<212> TYPE: PRT
<213> ORGANISM: Homo sapiens

<400> SEQUENCE: 29

Ser Gly Thr Ala Ser Ser Ile Ile Asp
1 5

<210> SEQ ID NO 30
<211> LENGTH: 9
<212> TYPE: PRT
<213> ORGANISM: Rattus sp.

<400> SEQUENCE: 30

Gly Val Ser Ala Ser Val Pro Val Glu
1 5

<210> SEQ ID NO 31
<211> LENGTH: 9
<212> TYPE: PRT
<213> ORGANISM: Rattus sp.

<400> SEQUENCE: 31

Pro Asp Ser Ala Pro Gly Glu Ile Glu
1 5

<210> SEQ ID NO 32
<211> LENGTH: 9
<212> TYPE: PRT
<213> ORGANISM: Rattus sp.

<400> SEQUENCE: 32

Asn Ile Ser Leu Val Gly Cys Ile Glu
1 5

<210> SEQ ID NO 33
<211> LENGTH: 9
<212> TYPE: PRT
<213> ORGANISM: Rattus sp.

<400> SEQUENCE: 33

Ile Asp Thr Ala Val Leu His Leu Asp
1 5

<210> SEQ ID NO 34
<211> LENGTH: 9
<212> TYPE: PRT
<213> ORGANISM: Rattus sp.

<400> SEQUENCE: 34

Thr Thr Ser Gly Val Pro Asp Leu Asp
1 5

<210> SEQ ID NO 35
<211> LENGTH: 9
<212> TYPE: PRT
<213> ORGANISM: Rattus sp.

<400> SEQUENCE: 35

Ile Pro Thr Val Asn Glu Asn Leu Glu
1 5

-continued

<210> SEQ ID NO 36
<211> LENGTH: 9
<212> TYPE: PRT
<213> ORGANISM: Homo sapiens

<400> SEQUENCE: 36

Ser His Ser Ala Val Cys His Leu Glu
1 5

<210> SEQ ID NO 37
<211> LENGTH: 9
<212> TYPE: PRT
<213> ORGANISM: Mus musculus

<400> SEQUENCE: 37

Ser Leu Ser Gly Val Cys His Leu Glu
1 5

<210> SEQ ID NO 38
<211> LENGTH: 9
<212> TYPE: PRT
<213> ORGANISM: Homo sapiens

<400> SEQUENCE: 38

Ser Phe Ser Pro Thr Cys Val Leu Glu
1 5

<210> SEQ ID NO 39
<211> LENGTH: 9
<212> TYPE: PRT
<213> ORGANISM: Mus musculus

<400> SEQUENCE: 39

Ser Phe Ser Pro Thr Cys Val Val Glu
1 5

<210> SEQ ID NO 40
<211> LENGTH: 9
<212> TYPE: PRT
<213> ORGANISM: Homo sapiens

<400> SEQUENCE: 40

Leu Gly Ser Gly Ser Thr Arg Leu Glu
1 5

<210> SEQ ID NO 41
<211> LENGTH: 9
<212> TYPE: PRT
<213> ORGANISM: Homo sapiens

<400> SEQUENCE: 41

Thr Phe Thr Ile Ser Tyr Asp Leu Glu
1 5

<210> SEQ ID NO 42
<211> LENGTH: 9
<212> TYPE: PRT
<213> ORGANISM: Mus musculus

<400> SEQUENCE: 42

Ser Phe Thr Ile Ser Tyr Asp Leu Glu
1 5

-continued

<210> SEQ ID NO 43
<211> LENGTH: 9
<212> TYPE: PRT
<213> ORGANISM: Homo sapiens

<400> SEQUENCE: 43

Asn Phe Ser Pro Thr Cys His Leu Asp
1 5

<210> SEQ ID NO 44
<211> LENGTH: 9
<212> TYPE: PRT
<213> ORGANISM: Homo sapiens

<400> SEQUENCE: 44

Gly Cys Thr Val Ser Pro Gln Val Glu
1 5

<210> SEQ ID NO 45
<211> LENGTH: 9
<212> TYPE: PRT
<213> ORGANISM: Rattus sp.

<400> SEQUENCE: 45

Val Thr Ser Leu Pro Arg Ala Met Asp
1 5

<210> SEQ ID NO 46
<211> LENGTH: 9
<212> TYPE: PRT
<213> ORGANISM: Homo sapiens

<400> SEQUENCE: 46

Asn Leu Ser Phe Ser Phe Arg Val Asp
1 5

<210> SEQ ID NO 47
<211> LENGTH: 9
<212> TYPE: PRT
<213> ORGANISM: Homo sapiens

<400> SEQUENCE: 47

Ser His Ser Phe Pro Ala Thr Leu Glu
1 5

<210> SEQ ID NO 48
<211> LENGTH: 9
<212> TYPE: PRT
<213> ORGANISM: Rattus sp.

<400> SEQUENCE: 48

Trp Pro Ser Leu Pro Ser Asn Met Asp
1 5

<210> SEQ ID NO 49
<211> LENGTH: 9
<212> TYPE: PRT
<213> ORGANISM: Rattus sp.

<400> SEQUENCE: 49

Phe Phe Ser Gly Ser Ser Gln Leu Glu
1 5

<210> SEQ ID NO 50
<211> LENGTH: 9

-continued

<212> TYPE: PRT
<213> ORGANISM: Rattus sp.

<400> SEQUENCE: 50

Trp Pro Ser Leu Pro Ser Gly Leu Asp
1 5

<210> SEQ ID NO 51
<211> LENGTH: 9
<212> TYPE: PRT
<213> ORGANISM: Homo sapiens

<400> SEQUENCE: 51

Gly His Ser Pro Pro Asp Asp Val Asp
1 5

<210> SEQ ID NO 52
<211> LENGTH: 9
<212> TYPE: PRT
<213> ORGANISM: Rattus sp.

<400> SEQUENCE: 52

Ser Val Thr Gly Ala Glu Glu Val Glu
1 5

<210> SEQ ID NO 53
<211> LENGTH: 9
<212> TYPE: PRT
<213> ORGANISM: Rattus sp.

<400> SEQUENCE: 53

Val Gln Thr Ala Val Thr Asn Ile Asp
1 5

<210> SEQ ID NO 54
<211> LENGTH: 9
<212> TYPE: PRT
<213> ORGANISM: Homo sapiens

<400> SEQUENCE: 54

Thr Arg Ser Gly Asn Cys Tyr Leu Asp
1 5

<210> SEQ ID NO 55
<211> LENGTH: 9
<212> TYPE: PRT
<213> ORGANISM: Homo sapiens

<400> SEQUENCE: 55

Asn Pro Thr Gly Val Gly Cys Val Asp
1 5

<210> SEQ ID NO 56
<211> LENGTH: 9
<212> TYPE: PRT
<213> ORGANISM: Homo sapiens

<400> SEQUENCE: 56

Gly Thr Thr Gly Cys Thr Asp Val Asp
1 5

<210> SEQ ID NO 57
<211> LENGTH: 9
<212> TYPE: PRT
<213> ORGANISM: Homo sapiens

-continued

<400> SEQUENCE: 57

Ser Ser Ser Gly Thr Glu Cys Leu Asp
1 5

<210> SEQ ID NO 58
<211> LENGTH: 9
<212> TYPE: PRT
<213> ORGANISM: Rattus sp.

<400> SEQUENCE: 58

Gly Val Thr Ala Ser Tyr Gly Val Glu
1 5

<210> SEQ ID NO 59
<211> LENGTH: 9
<212> TYPE: PRT
<213> ORGANISM: Rattus sp.

<400> SEQUENCE: 59

Phe Thr Thr Ala Pro Glu Asn Val Asp
1 5

<210> SEQ ID NO 60
<211> LENGTH: 9
<212> TYPE: PRT
<213> ORGANISM: Homo sapiens

<400> SEQUENCE: 60

Leu Lys Ser Ile Cys Glu Val Leu Asp
1 5

<210> SEQ ID NO 61
<211> LENGTH: 9
<212> TYPE: PRT
<213> ORGANISM: Rattus sp.

<400> SEQUENCE: 61

Ile Ser Ser Phe Cys Thr Val Val Asp
1 5

<210> SEQ ID NO 62
<211> LENGTH: 9
<212> TYPE: PRT
<213> ORGANISM: Bos taurus

<400> SEQUENCE: 62

Phe Gln Ser Phe Gly Arg Tyr Leu Glu
1 5

<210> SEQ ID NO 63
<211> LENGTH: 9
<212> TYPE: PRT
<213> ORGANISM: Rattus sp.

<400> SEQUENCE: 63

Ser Gly Thr Pro Val Asp Asp Leu Asp
1 5

<210> SEQ ID NO 64
<211> LENGTH: 9
<212> TYPE: PRT
<213> ORGANISM: Mus musculus

<400> SEQUENCE: 64

-continued

```
Asn Ile Thr Phe Ser Lys Gln Ile Glu
1               5


<210> SEQ ID NO 65
<211> LENGTH: 9
<212> TYPE: PRT
<213> ORGANISM: Homo sapiens

<400> SEQUENCE: 65

Ser Gly Ser Phe Thr Thr Ala Leu Asp
1               5


<210> SEQ ID NO 66
<211> LENGTH: 9
<212> TYPE: PRT
<213> ORGANISM: Rattus sp.

<400> SEQUENCE: 66

Val Gln Ser Leu Thr Cys Glu Val Asp
1               5


<210> SEQ ID NO 67
<211> LENGTH: 9
<212> TYPE: PRT
<213> ORGANISM: Rattus sp.

<400> SEQUENCE: 67

Leu Arg Ser Ile Asn Gln Gly Leu Asp
1               5


<210> SEQ ID NO 68
<211> LENGTH: 9
<212> TYPE: PRT
<213> ORGANISM: Homo sapiens

<400> SEQUENCE: 68

Val Met Ser Phe Val Asn Leu Val Glu
1               5


<210> SEQ ID NO 69
<211> LENGTH: 9
<212> TYPE: PRT
<213> ORGANISM: Homo sapiens

<400> SEQUENCE: 69

Val Met Ser Phe Val Asn Met Val Glu
1               5


<210> SEQ ID NO 70
<211> LENGTH: 15
<212> TYPE: PRT
<213> ORGANISM: Homo sapiens

<400> SEQUENCE: 70

Phe Phe Tyr Phe Phe Thr Gly Ser Ser Gln Leu Glu Phe Asp Pro
1               5                   10                  15


<210> SEQ ID NO 71
<211> LENGTH: 15
<212> TYPE: PRT
<213> ORGANISM: Homo sapiens

<400> SEQUENCE: 71

Ser Ala Phe Trp Pro Ser Leu Pro Ser Tyr Leu Asp Ala Ala Tyr
```

-continued 1 5 10 15

<210> SEQ ID NO 72
<211> LENGTH: 15
<212> TYPE: PRT
<213> ORGANISM: Homo sapiens

<400> SEQUENCE: 72

Gln Gly Thr Ile Asp Thr Ala Val Leu His Leu Asp Thr Asn Leu
1 5 10 15

<210> SEQ ID NO 73
<211> LENGTH: 15
<212> TYPE: PRT
<213> ORGANISM: Homo sapiens

<400> SEQUENCE: 73

Ser Ser Phe Trp Pro Ser Leu Pro Ser Gly Val Asp Ala Ala Tyr
1 5 10 15

<210> SEQ ID NO 74
<211> LENGTH: 15
<212> TYPE: PRT
<213> ORGANISM: Homo sapiens

<400> SEQUENCE: 74

Ser Tyr Arg Leu Arg Ser Pro Val Ile Ser Ile Asp Pro Pro Ser
1 5 10 15

<210> SEQ ID NO 75
<211> LENGTH: 15
<212> TYPE: PRT
<213> ORGANISM: Homo sapiens

<400> SEQUENCE: 75

Glu Asp Leu Val Gly Ser Ala Ser Gly Asp Leu Asp Leu Gly Lys
1 5 10 15

<210> SEQ ID NO 76
<211> LENGTH: 15
<212> TYPE: PRT
<213> ORGANISM: Homo sapiens

<400> SEQUENCE: 76

Gln Leu Leu Gly Val Ser Ala Ser Val Pro Val Glu His Arg Asp
1 5 10 15

<210> SEQ ID NO 77
<211> LENGTH: 15
<212> TYPE: PRT
<213> ORGANISM: Homo sapiens

<400> SEQUENCE: 77

Gln Pro Leu Val Gln Thr Ala Val Thr Asn Ile Asp Arg Pro Lys
1 5 10 15

<210> SEQ ID NO 78
<211> LENGTH: 15
<212> TYPE: PRT
<213> ORGANISM: Homo sapiens

<400> SEQUENCE: 78

Met Thr Ser Leu Lys Ser Val Asn Gly Gln Ile Glu Ser Leu Ile
1 5 10 15

-continued

```
<210> SEQ ID NO 79
<211> LENGTH: 15
<212> TYPE: PRT
<213> ORGANISM: Homo sapiens

<400> SEQUENCE: 79

Leu Gly Gly Ser Gly Thr Pro Val Asp Glu Leu Asp Lys Cys Cys
1               5                   10                  15


<210> SEQ ID NO 80
<211> LENGTH: 15
<212> TYPE: PRT
<213> ORGANISM: Homo sapiens

<400> SEQUENCE: 80

Thr Thr Thr Val Ser Ser Phe Ser Leu Asn Val Glu Tyr Ala Ile
1               5                   10                  15


<210> SEQ ID NO 81
<211> LENGTH: 15
<212> TYPE: PRT
<213> ORGANISM: Homo sapiens

<400> SEQUENCE: 81

Asn Ala Met Leu Lys Ser Ile Cys Glu Val Leu Asp Leu Glu Arg
1               5                   10                  15
```

PEPTIDES FOR THE TREATMENT, PROPHYLAXIS, DIAGNOSIS AND MONITORING OF AUTOIMMUNE DISEASES

FIELD OF THE INVENTION

The present invention relates to a method of identifying peptides useful for the treatment and monitoring of autoimmune diseases, especially arthritis, and to the peptides and proteins thus identified and their use in therapy and monitoring of the disease.

BACKGROUND ART

Autoimmune Diseases

One of the most intriguing characteristics of the immune system is its unlimited specificity. When threatened by potential dangerous foreign substances (antigens), including pathogens, the immune system mounts a tailor-made response. This tailor-made response is provided by the immune system's antigen specific T and B lymphocytes. The virtually unlimited repertoire provided by these immune cells calls for a tight regulatory system preventing unwanted responses against our own (self) antigens. For years it was thought that the immune system was able to discriminate between self and non-self. However, with the growing knowledge of immunology, this theory has become more and more unsatisfactory. The self/non-self paradigm does not explain why perfectly healthy individuals can have circulating autoreactive T and B cells without any symptoms of autoimmune diseases.

Recently, a new concept providing more satisfactory explanations for the lack of autoimmune reactions in healthy individuals has been developed. In this new hypothesis, the decision whether the immune system is activated does not solely depend on the recognition of an antigen as foreign, but also on the immune system's judgment whether it imposes danger to the integrity of the individual. The immune response must be considered as an outcome of a complex interaction between the lymphocyte and the antigen presenting cell (APC) in the context of cognate costimulatory signals, and the local cytokine microenvironment in which the recognition of the specific antigen takes place. This new view on the immune system does not only provide explanations for issues that made us doubt about the self/non-self paradigm, it also provides more insight in the mechanisms of central and peripheral tolerance. In the view of this new concept it is hypothesised that autoimmune diseases are the result of a qualitative or quantitative defect in the regulatory capacity of the immune system to control the naturally occurring autoreactive T-cell repertoire. It is therefore most important to develop novel therapeutic strategies for autoimmune diseases, such as rheumatoid arthritis, that aim at the reestablishment of such regulatory mechanisms of the immune system.

Rheumatoid Arthritis

Rheumatoid Arthritis (RA) is considered to be an autoimmune disease with chronic inflammation of the synovial membrane. RA is the most common inflammatory cause of disability in the western world. The prevalence of RA is approximately 1% of the population (range 0.3 to 2.1 percent); women are affected about three times more often than men. Specific characteristics of patients with RA are a variable degree of joint destruction and symmetric synovitis of their peripheral joints. Although the underlying cellular and molecular mechanisms have remained unclear until now, RA seems to provide a good example of how the interaction between genetic and environmental factors may lead to autoimmunity. Whilst environmental risk factors remain elusive, an association was found of RA with HLA-DR4 or a consensus sequence (QKRAA (SEQ ID NO: 1) or QRRAA (SEQ ID NO: 2)) in the hyper-variable region of the DRB1 molecule. Identification of the underlying cellular and molecular mechanisms leading to RA is complicated by the time of diagnosis. Since the moment of first symptoms is not known, by definition no patients with an early stage of the disease are available. When RA is diagnosed, it is a most destructive joint disease and its clinical course is characterised by involvement of the small joints of the hands and feet followed by centripetal progression to larger joints and finally even to the cervical spine. The histology of the disease is characterised by hyperplastic synovial tissue which is heavily infiltrated by various types of leucocytes. It is very likely that the constant supply of new cells of the immune system is necessary to induce and subsequently maintain the inflammatory process. Growing evidence for the involvement of T cells in RA is provided by the beneficial effect for RA patients from therapy that down regulates the effects of these lymphocytes.

The current treatments for RA are only symptomatic and can be divided into three lines. The first line of therapy consists of treatment with non-steroidal anti-inflammatory drugs (NSAIDs). These drugs can control pain and swelling of the joints, but do not halt the progressive joint destruction associated with the disease. Furthermore, NSAIDs can cause upper gastro-intestinal tract bleeding upon prolonged usage. Where RA remains active despite treatment with NSAIDs (which is usually the case), the second line of therapy can be applied, that consists of treatment with disease modifying anti-rheumatic drugs (DMARDs). These DMARDs, such as penicillamine, chloroquine, gold compounds and sulfasalazine, generally show some beneficial effect after a period of 3–6 months. However, due to severe side effects, treatment with DMARDs has to be stopped in about 25% of the patients. The belief that the immune system is actively involved in the onset and pathogenesis of RA has led to the development of a third line of treatment with strong broad-acting immunosuppressive drugs such as cyclosporin A and methotrexate. These strong immunosuppressive drugs generally have severe side effects, such as nephrotoxicity and in the long-term cancer. Besides the adverse side effects with the currently used anti-rheumatic drugs, the long-term outcome of sequential mono-therapy based on the therapeutic pyramid described above has been disappointing. No substantial evidence has been found proving that the currently used conventional drugs actually arrest the progression of joint destruction. Therefore, alternative strategies such as immunotherapy are clearly needed.

Optimal drugs for the treatment of autoimmune diseases such as RA would be able to attenuate the autoimmune process by re-establishing the immune system's self-regulatory mechanisms that have failed and resulted in the autoimmune attack. Treatment during the early phase of the autoimmune process with such drugs have the potential to arrest the disease process. It has been demonstrated that T cells play a central role in the auto-destructive process in RA (Sigall et al., *Clin. Exp. Rheum.* 6:59 (1988)). Treatments that selectively suppress the activity of such autoreactive T cells can therefore be preferred. Such treatment could consist of the administration of an autoantigen or peptides derived thereof. This type of treatment has been very successful in the suppression of disease symptoms in various experimental autoimmune disease models in laboratory animals (Cremer et al., *J. Immunol.* 131: 2995 (1983); Myers et al., *Immunol.* 90: 161 (1997)). Oral or nasal administration of type II collagen before induction of collagen-induced arthritis can prevent disease induction in this mouse model. However, it is unclear at present time whether native type II collagen is really involved in the primary pathogenesis of RA. Thus the real autoantigens that are the target for autoreactive T cells in RA and that can be used for the generation of a therapeutic formulation for the treatment of RA may not have been identified. Despite the discussion about the role of native type II collagen in the primary pathogenesis of RA, the above described results in animal models have been translated into clinical testing in humans. Initial clinical studies have suggested clinical efficacy of oral toleration for RA with chicken type II collagen (Trentham et al., *Science* 261: 1727 (1993)). However, recent results of a large phase III clinical study have shown that oral treatment with type II collagen does not result in statistical significant clinical benefit for RA patients. Other proteins have been proposed as relevant target antigen in rheumatoid arthritis. One of these, human cartilage glycoprotein 39 (WO 96/13517), was recently described as potentially useful for the treatment of rheumatoid arthritis.

A major problem in the evaluation of the efficacy of novel immunotherapies aiming at T cell modulation, is the lack of proper tools to isolate and characterise T cells at the clonal level. The current development of multimeric MHC/peptide carrier systems to bind and isolate T cells in an antigen specific fashion, however opens novel possibilities for evaluating changes in T cell responses during and after immunotherapy (Kozono et al., *Nature* 369: 151 (1994)).

SUMMARY OF THE INVENTION

The invention relates to peptides and proteins suitable for the prophylaxis, treatment, diagnosis and/or monitoring of autoimmune diseases, including arthritis, said peptide comprising a contiguous sequence of 9 amino acid residues (nonapeptide), wherein the peptides have been selected by compliance with the amino acid sequence X1-X2-X3-X4-X5-X6-X7-X8-X9, wherein X2, X6 and X7 are any amino acid, X1 is any amino acid except K,H,R,E,D;

X3 is S or T;

X4 is one of F,L,I,V,A,G,C,P;

X5 is one of A,G,C,P,S,N,T,V;

X8 is one of V,L,I,M;

X9 is E or D.

For peptides suitable in relation to arthritic conditions, X1 is in particular A, F, G, I, L, N, P, Q, S, T, V, W, and X4 is in particular F, L, I, V, A, G, P. The peptide should preferably be derived from a mammalian cartilage, joint or arthritis-related protein such as collagen or a cartilage protein, and be capable of being recognised by freshly isolated T cells from rats in which Adjuvant Arthritis is induced and/or be capable of being recognised in vitro by T cell clone A2b. These peptides as such and proteins containing them are candidates for the prophylaxis, treatment, diagnosis and monitoring of arthritis-like conditions. If the rat sequence differs from the human sequence, the human homologue peptide/protein is selected as well for studies in RA and JCA patients. Suitably the isolated T cells are A2b-like.

In addition to to the nonamer sequence, the peptides according to the invention may comprise further amino acids derived from the relevant protein at either side of the nonamer, especially up to 11 further amino acids. Most preferably, the peptide contains 12–18 amino acids from the relevant (autoimmune-related) protein.

Peptides which contain mutations, especially conserved mutations, in the selected sequence are also part of the invention, and can be useful in arthritis treatment and monitoring. Peptides which contain at least five, especially at least seven amino acid residues which are in the same relative position as the corresponding amino acids of the sequences selected as above are also claimed.

The invention further relates to a method of selecting these peptides and to the use of the peptides and proteins containing these sequences in the prophylaxis and treatment of arthritis and arthritis-related conditions. The invention also provides a pharmaceutical composition containing one or more peptides or proteins as described above, optionally together with stabilisers, excipients, adjuvants or the like, in a pharmacologically acceptable carrier, for prevention or treatment of autoimmune diseases, including arthritic conditions.

The invention also pertains to such peptides and proteins for use in diagnosis and monitoring of arthritis, for example by using such natural or mutated peptides or proteins as antigens in an immunoassay of a biological sample wherein the presence of antibodies against or T cell recognition of such peptides and proteins is measured. The immunoassay may be of the competition type, or of the sandwich type or any other suitable type, such as e.g. the use of multivalent MHC/peptide carriers to isolate and characterise T cells. The proteins, peptides or carriers may or may not be labelled by conventional labels. The invention also provides a diagnostic kit containing at least a peptide or protein as described above, for detecting and monitoring arthitis or arthritis-like conditions. The invention is also directed at MHC-peptide complexes of the peptides according to the invention and at the use thereof for monitoring, diagnosing or treating arthritis or arthritis-like conditions.

DETAILED DESCRIPTION OF THE INVENTION

Figure 1:
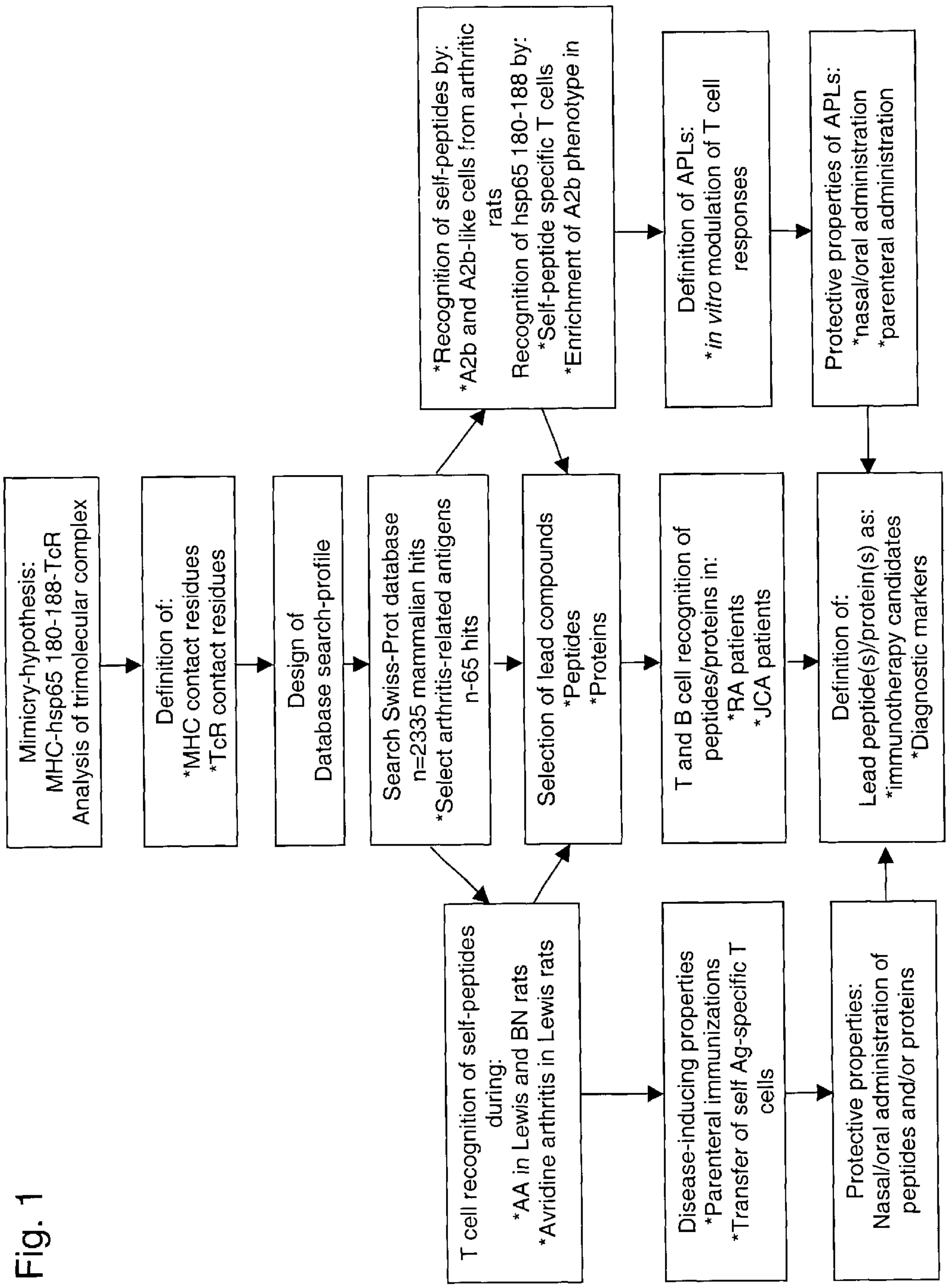
FIG. 1 shows an overview of the selection scheme for the definition of candidate arthritis-associated antigens that can serve as a target for autoimmune T-cell mediated tissue destruction in arthritis.

Immunisation of inbred Lewis rats with heat-killed *Mycobacterium tuberculosis* (MT) suspended in mineral oil results in an arthritis-like disease, characterised by inflammation of the synovium, formation of pannus, destruction of cartilage and erosion of bone (Pearson and Wood, *Arth. Rheum.* 2:440 (1959)). This is also known as the Adjuvant Arthritis (AA) model, first described by Pearson (*Proc. Soc. Exp. Biol. Med.* 91:95 (1956)). The A2b T-cell clone (Holoshitz et al., *Science* 219:56 (1983)) has been isolated from Lewis rats immunised with heat-killed MT and can induce arthritis when injected into naive Lewis rats. Based on this observation, Van Eden et al (*Proc. Natl. Acad. Sci. U.S.A.* 82:5117 (1985)) described that the A2b T-cell clone, generated with heat-killed MT as the immunising antigen, recognises a yet unidentified rat cartilage (associated) component. Later, the specific antigen of the A2b T-cell clone was identified as the MT heat shock protein 65 (hsp65) (Van Eden et al., *Nature* 331:171 (1988)), and the minimal core epitope was mapped from amino acid 180 to 186 (Van der Zee et al., *Eur. J. Immunol.* 19:43 (1989)). The A2b T-cell clone is a classical example of molecular mimicry, a T cell stimulated by a mycobacterial protein that recognises a self-protein, leading to severe tissue destruction.

Because the rat self-antigen to which the A2b T-clone is reactive is not known at present time, the present inventors have designed a computer search strategy based on the interactions of the mycobacterial hsp65 178–186 peptide within the trimolecular complex of MHC class II (RT1.$B^L$)-mycobacterial hsp65 178–186-T-cell receptor of clone A2b, to identify relevant candidate arthritis-associated antigens that can serve as target for autoimmune T-cell mediated tissue destruction in arthritis. Within the mycobacterial hsp65 178–186 sequence, residues involved in MHC binding have been identified by using an MHC-peptide binding assay on isolated MHC class II RT1.$B^L$ proteins. The residues which have an important role in determining the RT1.$B^L$ binding affinity of the mycobacterial hsp65 178–186 peptide, the so-called MHC anchor residues were determined. By studying the MHC-peptide binding affinities of other non-related peptides, a general MHC-peptide binding motif for the Lewis rat RT1.B1 molecule was defined (Wauben et al., *Int. Immunol.* 9:281 (1997)). For the definition of residues within the minimal core sequence mycobacterial hsp65 180–186, interacting with the T-cell receptor of the A2b T cell clone, the results derived from MHC-peptide binding assays, and proliferation assays of the A2b T cell clone were integrated. Based on these results 3 putative T-cell receptor contact residues could be identified within the MT hsp65 180–186 sequence.

The detailed design of the protein data-base search profile for the identification of relevant arthritis-associated antigens is described below in examples 1, 2 and 3. After searching the Swiss-Prot database, all mammalian hits were screened for joint (associated) proteins, and proteins which have been described previously to be involved in arthritic inflammatory processes. Of the 2335 mammalian hits, n=65 hits were selected as possible targets antigens. On the one hand these peptides are tested in vitro for recognition by T-cell clone A2b as measured by proliferation, cytokine production, T-cell receptor downregulation, expression of cell surface markers, anergy induction, and apoptosis. In addition, freshly isolated A2b-like cells from arthritic rats are evaluated in the same way. On the other hand T-cell lines specific for the selected peptides are generated after in vivo immunisation with these peptides, and cross-reactivity between the immunising agent and the MT hsp65 178–186 peptide is evaluated. The panel of n=65 peptides is tested as well, for T-cell recognition during the course of adjuvant arthritis and avridine (non-microbial) induced arthritis in the Lewis rat. Genetic promiscuity of these peptides is analysed by monitoring T-cell recognition during the course of adjuvant arthritis in Lewis- and in MHC discordant Brown Norway rats.

Besides the nonamer core sequence, as identified by the search profile, flanking residues of the native self T-cell epitope can be involved in T-cell receptor binding as well. Therefore recognition of synthetic peptides comprised of different length variants of the natural protein sequence (9–20 mers), but always containing the 9-mer core sequence as used for the search, is evaluated during the T-cell monitoring assays. Furthermore, disease-inducing capacities upon active immunisation in adjuvants and upon T-cell transfer studies of self-peptide specific T cells, as well as protective capacities upon nasal administration of the selected self peptides, is studied in the experimental rat models.

The protective effect of the selected peptides can be further improved by making altered peptide variants, as selected upon in vitro modulation of self-peptide specific T cells derived from arthritic rats. Furthermore, the therapeutic effects of peptides and altered peptide variants are compared with the effects using entire proteins and corresponding altered protein variants during the induction of mucosal tolerance either via the nasal or the oral route. The efficacy of the therapeutic effects will be improved by adding stabilising compounds to the peptides, as well as by adding specific targeting signals. Selected peptides and proteins are studied both for their efficacy to prevent (vaccination strategy) and to treat experimental arthritis. Peptides and/or proteins which are recognised during the experimental arthritis processes, are monitored for T-cell recognition in human RA, as well as in juvenile chronic arthritis (JCA) patients. Furthermore, human T-cell lines specific for selected self-antigens are generated, and the capacity of APLs (altered peptide ligands), either in the peptide- and the protein context, as defined in the rat system to modulate the response of the wild-type antigen, is tested in vitro. Based on these results candidates for immunotherapy of rheumatoid and juvenile chronic arthritis are selected. Furthermore, recognition of peptides and proteins during the experimental arthritis models, rheumatoid arthritis and juvenile chronic arthritis can be used as a diagnostic marker or monitor for arthritis, or arthritis-like diseases. The approach as described here can be applied for all mimicry concepts in autoimmunity e.g. role of viruses in diabetes or MS. An overview of the selection scheme for the definition of candidates is presented in FIG. 1.

EXAMPLES

Example 1

Definition of Search Profile for RT1.$B^L$-binding Self-peptides Based on the MHC-anchor Residues The inbred Lewis rat strain is extremely prone to experimental autoimmune diseases, in which autorcactive CD4+ T cells play a pivotal role. CD4+ T cells specifically bind with their T-cell receptor to a complex formed between a processed antigen fragment and the MHC class II molecule expressed on antigen presenting cells (APC). The RT1.$B^L$ MHC-peptide binding motif has recently been described (Wauben et al., *Int. Immunol.* 9:281 (1997)). Based on this extended MHC class II-peptide binding motif, a protein data base search profile for RT1.$B^L$ binding peptides was defined. In general, defined self-peptides involved in autoimmune diseases are intermediate to poor MHC binders (Joosten et al., *Int. Immunol.* 5:751 (1994)). Thus a search strategy for self-antigens involved in Adjuvant Arthritis should not specifically select for high affinity binders. However, a manageable number of hits must be selected. Based on these two criteria the following search profile for MHC-anchor residues was defined:

{K,H,R,E,D}-X-[S,T]-X-{H,R,K}-X-X-[V,L,I,M]-[E,D]

In this search profile for each position the allowed amino acids [ ] or the excluded amino acids { } are denoted in the single letter code, whereas X means that all amino acids are allowed at that position. At MHC anchor positions 3 and 9 only a limited number of amino acids are allowed, since both positions are required for intermediate to strong MHC binding. At the less stringent MHC anchor position 1 all hydrophilic charged residues are excluded because of their detrimental effect on RT1.$B^L$ binding, while at position 5 only positively charged residues have such a detrimental effect. To lower the number of hits generated with the search profile, the amino acids allowed at MHC anchor position 8 are reduced to the best fitting amino acids, as was tested in the peptide-MHC binding assay with substitution analogues of the mycobacterial hsp65 180–188 peptide on isolated RT1.$B^L$ molecules. At the remaining positions in the peptide, which were not affected in MHC binding affinity upon substitution analysis, all amino acids are allowed (indicated by X).

Example 2

Definition of Search Profile for Self-peptides Based on A2b TcR-contact Residues As described above, the A2b T-cell clone is the classical example of molecular mimicry: a T cell stimulated by a mycobacterial protein that recognises a self-antigen, leading to severe tissue destruction. Since the self-antigen that is recognised by the A2b T-cell clone until today has not been identified, a protein data base search profile was designed according to the T cell receptor-contact residues within the mycobacterial hsp65 180–188 epitope. The TcR-contact residues in the hsp65 180–188 peptide were identified by evaluating the proliferative responses of the A2b cells to a panel of synthetic peptide analogues of hsp65 180–188, and by combining these results with the peptide-MHC binding affinity. of the given peptide analogues and their inhibitory capacity of the wild-type peptide induced A2b response. This is exemplified by the experiments shown in Table 1.

Table 1

Analysis of the Proliferation-inducing and Inhibitory Capacity of Mycobacterial hsp65 180–188 Alanine Substitution Analogues, and Measurement of their Relative RT1.$B^L$ Binding Affinity

| | Proliferation of clone A2b* | Inhibition of clone A2b§ | MHC RT1.$B^L$ binding affinity# |
|---|---|---|---|
| hsp65 180–188: | | | |
| TFGLQLELT (SEQ ID NO: 3) | +++ | n.t. | 32–64 μM |
| Alanine substitution analogues: | | | |
| AFGLQLELT (SEQ ID NO: 4) | ± | | 64–128 μM |
| TAGLQLELT (SEQ ID NO: 5) | − | ++ | 64–128 μM |
| TFALQLELT (SEQ ID NO: 6) | − | + | 32–64 μM |
| TFGAQLELT (SEQ ID NO: 7) | − | ++++ | 8–16 μM |
| TFGLALELT (SEQ ID NO: 8) | − | − | >256 μM |
| TFGLQAELT (SEQ ID NO: 9) | ± | − | 32–64 μM |
| TFGLQLALT (SEQ ID NO: 10) | ± | − | 128–256 μM |
| TFGLQLEAT (SEQ ID NO: 11) | +++ | n.t. | 32–64 μM |
| TFGLQLELA (SEQ ID NO: 12) | +++ | n.t. | 32–64 vM |

*The proliferation-inducing capacity of the alanine substitution analogues as compared to the wild-type peptide hsp65 180–188 induced proliferation of T cell clone A2b.

§The inhibitory capacity of the alanine substitution analogues is measured in a competition assay in which clone A2b was stimulated with a suboptimal dose of wild-type peptide hsp65 180–188.

#RT1.$B^L$ binding affinity is expressed as 50%ID (=inhibitory dose). The 50%ID value indicates the concentration of peptide needed to inhibit 50% binding of the marker peptide in a competition assay on isolated RT1.$B^L$ molecules.

This analysis has revealed three putative TcR-contact residues in the mycobacterial hsp65 180–188 peptide; positions 181, 182 and 183. Although not comparable to the level of proliferation induced by the wild-type peptide 180–188, at positions 181 and 182 some of the substitutions, in particular conserved substitutions, could induce proliferation of T-cell clone A2b. For the search profile at positions 181 and 182 amino acids were selected which were related to the original residue or to a proliferation inducing substitution variant. At position 183 none of the tested amino acid substitutions could induce proliferation of A2b. Interestingly, introduction of substitutions at the TcR-contact residue on position 183 resulted in the generation of strong modulatory effects. We and others described previously, that substitutions at TcR contact residues within a T-cell epitope can result in modulatory variant peptides which are extremely potent in blocking the T-cell response against the wild-type peptide (Wauben et al. *J. Exp. Med.* 1992, 176:667–677). However, such altered peptide ligands (APL) can also result in a qualitatively changed T-cell response. Since self-peptides can function as APL's of bacterial peptides (and vice a versa), and since the exact rules for the design of such APLs are not known yet, the inventors decided that in the search profile the TcR contact residue at position 183 should not be restricted to any particular amino acid. The search profile based on the A2b TcR-MT hsp65 180–188 peptide contact residues was as follows:

X-[F,L,I,V,A,G,C,P]-[A,G,C,P,S,N,T,V]-X-X-X-X-X-X

In this search profile for each position the allowed amino acids [ ] are denoted in the single letter code, whereas X means that all amino acids are allowed at that position.

Example 3

Definition and Use of a Complete Search Profile for RT1.$B^L$-binding Peptides Based on the MHC-anchor Residues and A2b TcR-contact Residues Combining the search profiles of Examples 1 and 2 (note that Example 1 was based on sequence 178–186 and Example 2 on sequence 180–188), resulted in the complete search profile for the identification of relevant target antigens in adjuvant arthritis. The complete search profile was as follows:

{K,H,R,E,D}-X-[S,T]-[F,L,I,V,A,G,C,P]-[A,G,C,P,S,N,T,V]-X-X-[V,L,I,M]-[E,D]

In this search profile for each position the allowed amino acids [ ] or the excluded amino acids { } are denoted in the single letter code, whereas X means that all amino acids are allowed at that position. The search profile was used to search the Swiss-Prot data-base containing known protein sequences. This resulted in a total of 12,867 hits, of which 2335 hits were present in mammalian proteins. Thereof, n=65 hits were selected based on cartilage, joint and/or arthritis related expression, as searched via Medline for the correlation between the given protein and arthritis, joint, and/or cartilage. Primarily the rat sequence was selected. However, if the rat sequence of a certain protein was not available, the human sequence was compared with the mouse sequence, if both sequences full-filled the selection criteria both sequences were selected. If only one mammalian protein sequence was available, that sequence was selected. The n=65 hits are listed in Table 2.

Table 2

Selected Arthritis-associated Mammalian Hits Derived from the Swiss-Prot Database by Using a Combined MHC Class II (RT.$B^1$)-TcR (A2b) Peptide Contact Residue Search-profile

| | Rat sequence | Human sequence | Mouse sequence |
|---|---|---|---|
| (Pro)collagens | | | |
| (Pro)collagenα1(I) | n.a. | LKSLSQQIE (SEQ ID NO: 13) | LKSLSQQIE (SEQ ID NO: 13) |
| (Pro)collagenα1(II),α2(I) | n.a. | LKSLNNQIE (SEQ ID NO: 14) | LKSLNNQIE (SEQ ID NO: 14) |
| (Pro)collagenα1(III) | LKSVNGQIE (SEQ ID NO: 15) | — | — |
| (Pro)collagenα1(VII) | n.a. | IFSLTPVLD (SEQ ID NO: 16) | n.a. |
| (Pro)collagenα1(X) | n.a. | QASGSAIID (SEQ ID NO: 17) | QASGSAIME (SEQ ID NO: 18) |
| (Pro)collagenα2(V) | n.a. | LKSLSSQIE (SEQ ID NO: 19) | n.a. |
| Proteoglycans | | | |
| Aggrecan (1) | VGSASGALD (SEQ ID NO: 20) | — | — |
| Aggrecan (2) | LPSGGESLE (SEQ ID NO: 21) | — | — |
| Aggrecan (3) | LPSGGDDLE (SEQ ID NO: 22) | — | — |
| Perlecan | n.a. | LRSPVISID (SEQ ID NO: 23) | LRSPVISIE (SEQ ID NO: 24) |
| Versican | n.a. | QDTVSLTVD (SEQ ID NO: 25) | n.a. |
| Versican | n.a. | VSSFSLNVE (SEQ ID NO: 26) | n.a. |
| Versican | n.a. | AGTLSPHVE (SEQ ID NO: 27) | n.a. |
| Versican | n.a. | SASATYGVE (SEQ ID NO: 28) | n.a. |
| Versican | n.a. | SGTASSIID (SEQ ID NO: 29) | n.a. |
| Chondroitin sulf.PG-NG2 (1) | GVSASVPVE (SEQ ID NO: 30) | — | — |
| Chondroitin sulf.PG-NG2 (2) | PDSAPGEIE (SEQ ID NO: 31) | — | — |
| Chondroitin sulf.PG-NG2 (3) | NISLVGCIE (SEQ ID NO: 32) | — | — |
| Chondroitin sulf.PG-NG2 (4) | IDTAVLHLD (SEQ ID NO: 33) | — | — |
| Biglycan | TTSGVPDLD (SEQ ID NO: 34) | — | — |
| Lumican | IPTVNENLE (SEQ ID NO: 35) | — | — |
| Laminins | | | |
| Lamininα-1 (1) | n.a. | SHSAVCHLE (SEQ ID NO: 36) | SLSGVCHLE (SEQ ID NO: 37) |
| Lamininα-1 (2) | n.a. | SFSPTCVLE (SEQ ID NO: 38) | SFSPTCVVE (SEQ ID NO: 39) |
| Lamininα-1 (3) | n.a. | LGSGSTRLE (SEQ ID NO: 40) | LGSGSTRLE (SEQ ID NO: 40) |
| Lamininα-2 (1) | n.a. | TFTISYDLE (SEQ ID NO: 41) | SFTISYDLE (SEQ ID NO: 42) |
| Lamininα-2 (2) | n.a. | NFSPTCHLD (SEQ ID NO: 43) | NFSPTCHLD (SEQ ID NO: 43) |
| Lamininα-2 (5) | n.a. | GCTVSPQVE (SEQ ID NO: 44) | GCTVSPQVE (SEQ ID NO: 44) |

-continued

| | Rat sequence | Human sequence | Mouse sequence |
|---|---|---|---|
| Laminin-S | VTSLPRAMD (SEQ ID NO: 45) | — | — |
| Lamininγ-1 | n.a. | NLSFSFRVD (SEQ ID NO: 46) | NLSFSFRVD (SEQ ID NO: 46) |
| Stromelysins | | | |
| MMP-1 | n.a. | SHSFPATLE (SEQ ID NO: 47) | n.a. |
| MMP-3 (1) | WPSLPSNMD (SEQ ID NO: 48) | — | — |
| MMP-3 (2) | FFSGSSQLE (SEQ ID NO: 49) | — | — |
| MMP-10 | WPSLPSGLD (SEQ ID NO: 50) | — | — |
| MMP-16 | n.a. | GHSPPDDVD (SEQ ID NO: 51) | n.a. |
| Calpain-2 | SVTGAEEVE (SEQ ID NO: 52) | — | — |
| Fibronectin | VQTAVTNID (SEQ ID NO: 53) | — | — |
| Fibrillins | | | |
| Fibrillin-1 | n.a. | TRSGNCYLD (SEQ ID NO: 54) | n.a. |
| Fibrillin-2 (1) | n.a. | NPTGVGCVD (SEQ ID NO: 55) | n.a. |
| Fibrillin-2 (2) | n.a. | GTTGCTDVD (SEQ ID NO: 56) | n.a. |
| Fibrillin-2 (3) | n.a. | SSSGTECLD (SEQ ID NO: 57) | n.a. |
| Bone sialoprotein II | GVTASYGVE (SEQ ID NO: 58) | — | — |
| Ceruloplasmin | FTTAPENVD (SEQ ID NO: 59) | — | — |
| Dek-protein | n.a. | LKSICEVLD (SEQ ID NO: 60) | n.a. |
| Fibromodulin | ISSFCTVVD (SEQ ID NO: 61) | — | — |
| Chondroadherin | n.a. | n.a. | FQSFGRYLE # (SEQ ID NO: 62) |
| Phospholipase-A2 | SGTPVDDLD (SEQ ID NO: 63) | — | — |
| Hyaluronic acid receptor | n.a. | n.a. | NITFSKQIE (SEQ ID NO: 64) |
| Tenascin | n.a. | SGSFTTALD (SEQ ID NO: 65) | — |
| Vimentin | VQSLTCEVD (SEQ ID NO: 66) | — | — |
| α-2 Macroglobulin receptor-associated protein | LRSINQGLD (SEQ ID NO: 67) | — | — |
| Bone morphogenetic protein 5,7 | n.a. | VMSFVNLVE (SEQ ID NO: 68) | VMSFVNLVE (SEQ ID NO: 68) |
| Bone morphogenetic protein 8 | n.a. | VMSFVNMVE (SEQ ID NO: 69) | VMSFVNMVE (8a) (SEQ ID NO: 69) |

* The numbers refer to the SEQ ID NO.'s

Bovine sequence n.a.: sequence not available

Example 4

T-cell Recognition of the Selected Peptides During Experimental Arthritis

Self peptides from the selected panel of 65 nonamer peptides are synthesised and tested for T-cell recognition during adjuvant arthritis and avridine arthritis in Lewis rats, as well as during adjuvant arthritis in (MHC discordant) BN rats. Information on the nature of the T-cell responses is collected by monitoring T-cell responses along the course of experimental arthritis. It is essential to monitor both mycobacterially induced (AA) and avridine (non-microbial) induced disease. Genetic promiscuity of the peptides is analysed by comparing T-cell responses in Lewis and (MHC discordant) BN rats. Of the n=65 peptides tested in a time course experiment in adjuvant arthritis in Lewis rats, n=20 peptides (SEQ ID NOs: 20, 21, 22, 23, 24, 30, 31, 33, 35, 36, 38, 40, 47, 49, 50, 51, 53, 54, 63, 65) were considered positive. The selection criteria used were: In more than 25% of the organs (inguinal and popliteal lymph nodes and spleen) tested, the pro-liferation induced by a given peptide must be more than 1.5 times the background of the assay. Proliferative responses were tested at days 14, 19, 21, 32, and 39 after disease induction with Mycobacterium tuberculosis in IFA.

Example 5

Recognition of the Selected Peptides by the A2b T-cell Clone and Freshly Isolated A2b-like T Cells from Arthritic Rats (Molecular Mimicry, Concept)

As an immediate read-out for mimicry peptides T-cell activation is measured by proliferation, TcR downregulation, expression of activation markers, and cytokines responses of clone A2b. In addition A2b-like T cells from arthritic rats are isolated, and activation of such cells is measured by, proliferation, TcR downregulation, expression of activation markers, and cytokines responses. Furthermore, T-cell lines are generated after immunisation with MT/IFA or selected peptides/DDA. The cross-reactive nature of the peptide specific T-cell responses is analysed in vitro by determining the recognition of both the self peptide as well as the mycobacterial hsp65 178–186 peptide. After testing the panel of n=65 peptides for induction of proliferation of T cell clone A2b, and/or induction of expression of activation markers, n=20 peptides (SEQ ID NOs: 15, 19, 20, 21, 22, 23, 24, 26, 30, 31, 32, 33, 35, 49, 51, 61, 63, 65, 67, 69) were considered positive. Criteria for positivity were that in 2 out of 4 experiments the induced proliferation was more than 2 times background proliferation as measured by $^3$H-thymidine incorporation, and/or that in 2 out of 3 experiments upregulation of an activation marker was detectable by FACS analysis.

Example 6

Recognition of the Selected Peptides/proteins by Human T Cells Obtained from RA/JCA Patients T-cell responses to the selected peptides in patients are analysed by studying T-cell proliferation of peripheral blood lymphocytes (PBL) and synovial fluid derived cells. Table 3 shows a typical example of an assay performed on PBLs derived from n=39 Rheumatoid arthritis (RA) patients and n=6 oligoarticular juvenile chronic arthritis (JCA) patients with some peptides (n=12) from Table 2, in which different response patterns can be seen. In these human studies the peptides are tested as 15-mers containing the 9-mer sequence of Table 2 as core sequence. The fact that all 12 peptides are being recognised in patients, demonstrates a certain promiscuity for MHC binding of the selected peptides. This is further strengthened by the fact that, the patients were not selected for having a certain MHC haplotype. The MHC binding affinity of the selected peptides is analysed for the most-common MHC class II-arthritis associations. In Table 3 the peptide binding affinity for DRB1*0401 is shown as an example. The peptide binding affinity is tested in a MHC-peptide competition assay on isolated MHC molecules in the presence of a labelled marker peptide. The fact that of the n=12 peptides selected for binding to the rat DQ equivalent $RT1.B^1$, n=11 peptides also bind DRB1*0401, further confirms the promiscuous MHC binding of the selected peptides. This ensures a wide applicability of the peptides for prophylaxis, treatment, monitoring and/or diagnosis of the disease.

Furthermore, besides proliferation induction, T cells are analysed for peptide induced cytokine production. Peptides which are recognised by RA/JCA patients are selected. To circumvent the possible limitations imposed on peptides by MHC restriction, despite the described promiscuity for MHC binding, it may be of advantage to have proteins or larger fragments of peptides available. For the analysis of the functional characteristics of such proteins in arthritis the genes of such proteins are cloned and expressed. The proteins are expressed in a prokaryotic system as well as in an eukaryotic expression systems providing for post-translational modifications. The purified recombinant proteins are used as antigens to monitor T-cell responses (rats and patients), and B cell responses. The analysis of T- and B-cell responses to the expressed proteins in both RA (adult) and JCA patients is correlated with the clinical status of the patients. Both severe advanced and remitting cases are tested. The recognition pattern of the self-antigens can be used as diagnostic marker for arthritic processes.

Peptides which are recognised by RA/JCA patents are used for preparing peptide/MHC complexes coupled to carrier systems. Such multivalent peptide/MHC carrier systems are used to identify and/or isolate and characterise T cells in an antigen-specific manner. The identification and characterisation of the antigen-specific T cells can be used for monitoring and diagnosing arthritis or arthritis-like conditions.

Table 3

Recognition of Arthritis-associated Peptides in RA and JCA Patients, and the Binding Affinity of the Peptides for DRB1*0401

| Tested peptides | RA patients (n = 39 tested) | JCA patients (n = 6 tested) | DRB1*0401 binding# (IC50 in μM) |
|---|---|---|---|
| MMP-3 (2): FFYFFTGSSQLEFDP (SEQ ID NO: 70) | 29^ | 2 | 0–8 |
| MMP-10: SAFWPSLPSYLDAAY (SEQ ID NO: 71) | 4 | — | 8–16 |
| Chondroitin sulf.(4): QGTIDTAVLHLDTNL (SEQ ID NO: 72) | 4 | 2 | 8–16 |
| MMP-3 (1): SSFWPSLPSGVDAAY (SEQ ID NO: 73) | 4 | — | 16–32 |
| Perlecan: SYRLRSPVISIDPPS (SEQ ID NO: 74) | 3 | 1 | 16–32 |
| Aggrecan (1): EDLVGSASGDLDLGK (SEQ ID NO: 75) | 2 | 2 | 32–64 |
| Chondroitin sulf.(1): QLLGVSASVPVEHRD (SEQ ID NO: 76) | 2 | — | 32–64 |
| Fibronectin: QPLVQTAVTNIDRPK (SEQ ID NO: 77) | 3 | — | 32–64 |

-continued

| Tested peptides | RA patients (n = 39 tested) | JCA patients (n = 6 tested) | DRB1*0401 binding# (IC50 in $\mu$M) |
|---|---|---|---|
| (Pro)collagen α1(III): MTSLKSVNGQIESLI (SEQ ID NO: 78) | 3 | — | 64–128 |
| Phospholipase A2: LGGSGTPVDELDKCC (SEQ ID NO: 79) | 1 | 1 | 128–256 |
| Versican: TTTVSSFSLNVEYAI (SEQ ID NO: 80) | 4 | 1 | 128–256 |
| Dek-protein: NAMLKSICEVLDLER (SEQ ID NO: 81) | 2 | 1 | >256 |

* The numbers refer to tire SEQ ID NO.'s

^ Indicated are the numbers of patients responding to tire peptides as defined in a 6-days proliferation assay on PBLs. Responses were considered positive if the proliferation (as measured by $^3$H-thymidine incorporation) was >2 times background proliferation. Peptides were tested in concentrations of 1 $\mu$g/ml and 10 $\mu$/ml.

MHC-peptide binding was measured as described in Wauben et al., *Int. Immunol.* 9:281 (1997). In short, detergent solubilised DRB1*0401 molecules (1 $\mu$M) were incubated with a standard concentration of biotinylated HA-marker peptide (100 nM) and a concentration range (0–256 $\mu$M) of the desired peptide. Peptide binding is expressed as tire IC50. IC50 is the dose of peptide needed to inhibit 50% binding of tire marker peptide. IC50 values between 0–64 $\mu$M represent good binders, between 64–256 $\mu$M intermediate binders, and >256 $\mu$M poor or non-binders.

Example 7

Disease-inducing Properties of the Selected Arthritis-associated Peptides/proteins To check the arthritogenic potential of the selected peptides, rats are immunised with 50 $\mu$g peptide in 100 $\mu$l DDA adjuvant in one hind footpad. Table 4 shows the arthritogenic capacity of 5 peptides from Table 2. Two of the five peptides show defined clinical arthritis.

Table 4

Disease Inducing Properties of Selected Arthritis-associated Peptides

| Selected peptides | Arthritis Induction* | DTH reaction# |
|---|---|---|
| Collagen α1(III): LKSVNGQIE (SEQ ID NO: 15) | 0/4 | 2/2 |
| Versican: VSSFSLNVE (SEQ ID NO: 26) | 0/4 | 2/2 |
| MMP-3 (1): WPSLPSNMD (SEQ ID NO: 48) | 1/4 | 0/2 |
| MMP-10: WPSLPSGLD (SEQ ID NO: 50) | 2/4 | 0/2 |
| Fibronectin: VQTAVTNID (SEQ ID NO: 53) | 0/4 | 2/2 |

* Arthritis is induced by Immunisation of 50 $\mu$g peptide in 100 $\mu$l DDA adjuvants in one hind footpad and scored upon clinical examination.

DTH (Delayed type hypersensitivity) reactions are induced at day 72 after immunisation of peptide/DDA, by subcutaneous injection of the peptide/saline in the ear. DTH are measured 24 and 48 hr after challenge.

Also passive transfer experiments of T cells specific for the self peptides are performed to analyse the in vivo activities of the responding T cells, and to evaluate the disease-inducing potential. From rats immunised with the peptides T cells are isolated from lymphoid tissues, activated in vitro and injected into naive rats. Besides peptides also the purified recombinant proteins are tested for their potential to induce arthritis.

Example 8

Protective Properties of Peptides/proteins Upon Nasal/oral Administration

The potential arthritis protective qualities of selected peptides/proteins are tested through nasal or oral tolerance induction in the adjuvant arthritis model. Table 5 shows a typical example of peptide based intervention in adjuvant arthritis upon nasal peptide administration. Of the 4 peptides tested the collagen α1(III) peptide (SEQ ID NO: 15) shows a protective effect.

Table 5
Protective Properties of Selected Arthritis-associated Peptides in the Adjuvant Arthritis Model Upon Nasal Administration

| Selected peptides | Day of onset* | Arthritis score* |
|---|---|---|
| Collagen α1(III): LKSVNGQIE (SEQ ID NO: 15) | 15.0 ± 1.7 | 4.3 ± 4.8 |
| Versican: VSSFSLNVE (SEQ ID NO: 26) | 13.0 ± 0 | 11.0 ± 3.5 |
| MMP-3 (1): WPSLPSNMD (SEQ ID NO: 48) | 13.3 ± 1.0 | 10.5 ± 1.7 |
| MMP-10: WPSLPSGLD (SEQ ID NO: 50) | 14.3 ± 2.0 | 11.3 ± 3.8 |

* Adjuvant arthritis is induced at day 0 by immunisation of MT/IFA (5 mg/ml MT) at the base of the tail. At days 0, 3, 7 and 11, 100 μg peptide in 10 μl saline is administered in the nostrils. Arthritis is scored upon clinical examination on a scale from 0–16. Data are expressed as mean±sd (n=4 rats/group).

Besides intervention in the adjuvant arthritis model in Lewis rats, intervention in the avridine induced arthritis in Lewis rats, as well as the adjuvant induced arthritis in the BN rats is tested.

Example 9

Generation and in vivo Testing of Peptide/protein Modifications (APL/PM)

Previously, we have shown that the anti-arthritogenic action of the MT hsp65 180–188 upon nasal application could be greatly improved by introducing a substitution at position 183 of the peptide (L→A). The mode of action of such altered peptide ligands (APL) is not yet fully understood, but their efficacy in several experimental autoimmune models is very good. T-cell effector functions can be directed at a molecular level through qualitative aspects of the TcR ligand, which is the peptide as presented in the context of the MHC. By selected mutations at the peptide aminoacid residues that interact with the TcR, it is possible to generate peptides that have T-cell modulatory activities (so-called APLs or altered peptide ligands). Parsimoneous Mutagenesis (PM) is a technique where whole proteins are being modified in the APL direction by a semi-directed introduction of conservative substitutions along the protein sequence (WO 97/30150). T-cells with specificity for lead peptides are used for the molecular definition of the peptides in terms of MHC and TcR-contact residues. Peptide modifications are designed on the basis of recognition by specific T-cell lines and MHC binding qualities. Mutated recombinant proteins are generated by the PM-method in which proteins are substituted at a desired frequency, e.g. 1-in-10-hit mutation, with a desired mutation, e.g. only conserved substitutions.

In vitro effects of peptide and protein modifications are analysed on peptide specific T-cell lines derived from rats or human patients. T cells are tested for proliferation, cell surface marker expression, anergy, apoptosis, and cytokine production. Furthermore, in cellular co-culture assays regulatory effects of T cells stimulated with APLs or PM-proteins are tested on other T-cell lines either specific for the wild-type peptide or specific for another non-related ligand.

APLs and PM-proteins are tested for their capacity to induce peripheral tolerance upon parenteral, oral or nasal administration. The therapeutic effects are evaluated during arthritis induction (prevention, vaccination-strategy) and during the course of the disease (treatment strategy). Furthermore, self-peptide specific T cells which have been defined to transfer disease, are tested for their capacity to transfer the disease upon in vitro restimulation with APLs or PM-protein.

What is claimed is:

1. A peptide suitable for the prophylaxis, treatment, diagnosis or monitoring of arthritis or an arthritic condition, wherein said peptide comprises amino acids 1 to 15 of SEQ ID NO:70, wherein said peptide has a length of 15–20 amino acids, wherein said peptide is recognised by T cells isolated from rats in which Adjuvant Arthritis is induced, or wherein said peptide is recognised in vitro by T cells that induce arthritis in a rat, or both, and wherein said peptide is bound by DRB1*0401.

2. A method of preventing or treating arthritis or an arthritis-like condition in a subject susceptible to or having arthritis or an arthritis-like condition, said method comprising administering to said subject a prophylactically- or therapeutically-effective amount of (i) a peptide comprising a contiguous sequence of 9 amino acid residues (nonapeptide) having the amino acid sequence X1-X2-X3-X4-X5-X6-X7-X8-X9, wherein (a)

X2, X6 and X7 are any amino acid,

X1 is one of A, F, G, I, L, N, P, Q, S, T, V, W,

X3 is S or T,

X4 is one of F, L, I, V, A, G, P,

X5 is one of A, G, C, P, S, N, T, V,

X8 is one of V, L, I, M,

X9 is E or D, (b) said nonapeptide is part of a mammalian cartilage protein, joint protein or arthritis-related protein, (c) said peptide has a length of 9–20 amino acids, and (d) said peptide is recognised by T cells isolated from rats in which Adjuvant Arthritis is induced, or wherein said first peptide is recognised in vitro by T cells that induce arthritis in a rat, or both, or (ii) a protein comprising said peptide, as an active ingredient, thereby preventing or treating arthritis or an arthritis-like condition in said subject.

3. A method of diagnosing arthritis or an arthritis-like condition in a subject susceptible to or having arthritis or an arthritis-like condition, said method comprising (a) combining (i) a peptide comprising a contiguous sequence of 9 amino acid residues (nonapeptide) having the amino acid sequence X1-X2-X3-X4-X5-X6-X7-X8-X9, wherein (aa)

X2, X6 and X7 are any amino acid,

X1 is one of A, F, G, I, L, N, P Q, S, T, V, W,

X3 is S or T,

X4 is one of F, L, I, V, A, G, P,

X5 is one of A, G, C, P, S, N, T, V,

X8 is one of V, L, I, M,

X9 is E or D, (bb) said nonapeptide is part of a mammalian cartilage protein, joint protein or arthritis-related protein, (cc) said peptide has a length of 9–20 amino acids, and (dd) said peptide is recognised by T cells isolated from rats in which Adjuvant Arthritis is induced, or wherein said peptide is recognised in vitro by T cells that induce arthritis in a rat, or both, or (ii) a protein comprising said peptide, with a biological sample obtained from said subject, wherein said sample contains an antibody or a T cell, or both, and (b) detecting an interaction between said peptide or said protein and an antibody, or between said peptide or said protein and a T cell, thereby diagnosing arthritis or an arthritis-like condition in said subject.

4. A method of preventing or treating arthritis or an arthritis-like condition in a subject susceptible to or having arthritis or an arthritis-like condition, said method comprising administering to said subject a prophylactically- or therapeutically-effective amount of a labelled or unlabelled peptide-MHC complex as an active ingredient, wherein (i) said peptide comprises a contiguous sequence of 9 amino acid residues (nonapeptide), and said nonapeptide:

(a) has the amino acid sequence X1-X2-X3-X4-X5-X6-X7-X8-X9, wherein

X2, X6 and X7 are any amino acid,

X1 is one of A, F, G, I, L, N, P, Q, S, T, V, W,

X3 is S or T,

X4 is one of F, L, I, V, A, G, P,

X5 is one of A, G, C, P, S, N, T, V,

X8 is one of V, L, I, M,

X9 is E or D, and (b) is part of a mammalian cartilage protein, joint protein or arthritis-related protein, (ii) said peptide has a length of 9–20 amino acids, and (iii) said peptide is recognised by T cells isolated from rats in which Adjuvant Arthritis is induced, or wherein said peptide is recognised in vitro by T cells that induce arthritis in a rat, or both, thereby preventing or treating arthritis or an arthritis-like condition in said subject.

5. A method of diagnosing arthritis or an arthritis-like condition in a subject susceptible to or having arthritis or an arthritis-like condition, said method comprising (a) combining a labeled or unlabelled peptide-MHC complex, wherein (i) said peptide comprises a contiguous sequence of 9 amino acid residues (nonapeptide), and said nonapeptide:

(aa) has the amino acid sequence X1-X2-X3-X4-X5-X6-X7-X8-X9, wherein

X2, X6 and X7 are any amino acid,

X1 is one of A, F, G, I, L, N, P, Q, S, T, V, W,

X3 is S or T,

X4 is one of F, L, I, V, A, G, P,

X5 is one of A, G, C, P, S, N, T, V,

X8 is one of V, L, I, M,

X9 is E or D, and (bb) is part of a mammalian cartilage protein, joint protein or arthritis-related protein, (ii) said peptide has a length of 9–20 amino acids, and (iii) said peptide is recognised by T cells isolated from rats in which Adjuvant Arthritis is induced, or wherein said peptide is recognised in vitro by T cells that induce arthritis in a rat, or both, with a biological sample obtained from said subject, wherein said sample contains an antibody or a T cell, or both, and (b) detecting an interaction between said peptide and an antibody or between said peptide and a T cell, thereby diagnosing arthritis or an arthritis-like condition in said subject.

6. The peptide according to claims 1, wherein said T cells that induce arthritis in a rat are A2b T cells.

7. The peptide according to claim 1, wherein said peptide is further recognised by peripheral blood lymphocytes (PBLs) of rheumatoid arthritis (RA) and/or juvenile chronic arthritis (JCA) patients.

8. A pharmaceutical composition comprising one or more peptides according to claim 1 and a pharmaceutically-acceptable carrier.

9. An MHC-peptide complex, said complex comprising a peptide according to claim 1.

10. The method according to claim 2, 3, 4 or 5, wherein the T cells that induce arthritis in a rat are A2b T cells.

11. The method according to claim 2, 3, 4 or 5, wherein said peptide is further recognised by peripheral blood lymphocytes (PBLs) of rheumatoid arthritis (RA) and/or juvenile chronic arthritis (JCA) patients.

12. The method according to claim 2, 3, 4 or 5, wherein said peptide is bound by DRB1*0401.

13. The method according to claim 2, 3, 4 or 5, wherein from one up to three of the amino acids X1–X9 have been mutated by conservative substitutions with respect to the amino acid sequence of said arthritis-related protein.

14. The method according to claim 13, wherein said mutation has been performed by Parsimoneous Mutagenesis.

* * * * *